(12) United States Patent
Iwata et al.

(10) Patent No.: US 7,182,862 B2
(45) Date of Patent: *Feb. 27, 2007

(54) FRACTIONATING APPARATUS

(75) Inventors: Yosuke Iwata, Kyoto (JP); Hiroyuki Fukuda, Yokohama (JP)

(73) Assignee: Shimadzu Corporation, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/030,394

(22) Filed: Jan. 5, 2005

(65) Prior Publication Data

US 2005/0158215 A1 Jul. 21, 2005

(30) Foreign Application Priority Data

Jan. 19, 2004 (JP) ............................. 2004-009927

(51) Int. Cl.
*B01D 15/08* (2006.01)

(52) U.S. Cl. ................. 210/198.2; 210/656; 210/101; 422/70; 250/288

(58) Field of Classification Search ................ 422/70; 250/288; 436/161, 173; 210/101, 198.2, 210/656

See application file for complete search history.

(56) References Cited

U.S. PATENT DOCUMENTS

| 4,977,785 | A | * | 12/1990 | Willoughby et al. ...... 73/863.12 |
|---|---|---|---|---|
| 5,477,048 | A | * | 12/1995 | Nakagawa et al. ......... 250/288 |
| 5,674,288 | A | * | 10/1997 | Knapp et al. ............ 623/11.11 |
| 5,690,828 | A | * | 11/1997 | Clay et al. ................... 210/634 |
| 6,462,334 | B1 | * | 10/2002 | Little et al. ................. 250/281 |
| 6,707,037 | B2 | * | 3/2004 | Whitehouse ................ 250/288 |
| 6,709,632 | B2 | * | 3/2004 | Nakagawa et al. ........... 422/54 |
| 6,800,849 | B2 | * | 10/2004 | Staats ......................... 250/288 |
| 6,803,568 | B2 | * | 10/2004 | Bousse et al. ............. 250/288 |
| 6,812,458 | B2 | * | 11/2004 | Gregori et al. ............ 250/288 |
| 6,977,369 | B2 | * | 12/2005 | Yamaguchi et al. ........ 250/281 |
| 2002/0187073 | A1 | * | 12/2002 | Moon et al. .................. 422/70 |
| 2004/0113068 | A1 | * | 6/2004 | Bousse et al. ............. 250/288 |
| 2004/0238427 | A1 | * | 12/2004 | Maruyama et al. ...... 210/198.2 |
| 2005/0147536 | A1 | * | 7/2005 | Iwata ......................... 422/100 |
| 2005/0158215 | A1 | * | 7/2005 | Iwata et al. ................. 422/101 |

FOREIGN PATENT DOCUMENTS

JP 3099866 12/2003

OTHER PUBLICATIONS

Machine Translation of Japan Patent No. 3099866, pp. 1-2 of claims and pp. 1-5 of detailed description.*
U.S. Appl. No. 11/030,393, filed Jan. 5, 2005, Iwata.

* cited by examiner

*Primary Examiner*—Ernest G. Therkorn
(74) *Attorney, Agent, or Firm*—Rankin, Hill, Porter & Clark LLP

(57) ABSTRACT

The probe has a triple tube structure, in which an eluate from a liquid chromatograph flows through an innermost flow passage, a matrix solution flows through a flow passage outside the innermost flow passage, and the air or acetone flows through an outermost flow passage. Before analysis, acetone is flowed to rinse the matrix compound deposited in the previous analysis and clean the tip portion of the probe, and then the air is flowed to evaporate the rinsing solution.

6 Claims, 2 Drawing Sheets

FRACTIONATING APPARATUS

BACKGROUND OF THE INVENTION

1. Field of the Invention

The present invention relates to a fractionating apparatus comprising a probe for dripping a sample liquid fed from a liquid feed mechanism such as an HPLC (High Performance Liquid Chromatograph), with an additive agent solution, from a tip portion of the probe onto a plate such as a microplate or sample plate to move a sample, in which the fractionating apparatus prepares the sample to be analyzed by MALDI-TOF-MS (Matrix Assisted Laser Desorption Ionization Time-Of-Flight Mass Spectrometry).

2. Description of the Related Art

In the field of a proteohm analysis for elucidating the structure or action of protein or peptide, the MALDI-TOF-MS, which has lately gained attention, is employed for analysis. The MALDI-TOF-MS is a method for adding a matrix solution to a biosample and drying it to have a sample, then applying laser beam to the sample and ionizing it, and making the mass spectroscopy, in which the used amount of sample is as small as several µL.

A fat-soluble material is employed as the matrix compound, and a matrix solution is produced by dissolving the matrix compound in a solvent at high concentration. The matrix compound is excellently dissolved in an organic solvent of acetonitrile. However, in the case where the biosample is separated and eluted by the liquid chromatograph, the matrix solution is added simultaneously, and the sample solution is dripped for fractionation, the fractionation time is usually 10 minutes or more. Since the matrix solution of high concentration is always contact with the atmosphere at the tip portion of the probe, the solvent evaporates with the passage of time, so that the matrix compound deposits at the tip portion of the probe.

When the matrix compound deposits at the tip portion of the probe, the distance between the tip portion of the probe and the sample plate is not kept constant, and the dripping position is not determined, whereby it is difficult to produce the uniform liquid droplet.

Moreover, the measurement constituents separated and eluted from the HPLC are taken into the deposited matrix, making the analysis incorrect.

Therefore, in the related art, before dripping for fractionation, the tip portion of the probe is manually rinsed with a solvent of acetone, using a cylinder, to remove the matrix compound deposited at the tip portion of the probe.

The operation for manually washing the tip portion of the probe before fractionation operation is troublesome, and poor in workability.

SUMMARY OF THE INVENTION

Thus, it is an object of the invention to provide a fractionating apparatus for automatically rinsing away the deposit at the tip portion of the probe when the additive agent solution is added.

The present invention provides a fractionating apparatus comprising a probe for dripping a sample liquid fed from a liquid feed mechanism such as a liquid chromatograph, with an additive agent solution, from a tip portion of the probe onto a plate. In the fractionating apparatus, the probe comprises a rinsing solution flow passage for feeding a rinsing solution dissolving the deposit from the additive agent solution to the tip portion at any time.

In a preferred form, the tip portion of the probe has a triple tube structure, in which the sample solution flows through the innermost tube, the additive agent solution flows through an intermediate tube outside it, and the outermost tube is the rinsing solution flow passage. The probe may have a gas supply flow passage for supplying a gas to the tip portion to dry the tip portion at any time.

In a preferred form of this case, the tip portion of the probe has a triple tube structure, in which the sample solution flows through the innermost tune, the additive agent solution flows through an intermediate tube outside it, and the outermost tube is used as the rinsing solution flow passage and the gas supply flow passage.

One example of the additive agent solution is a solution of matrix compound for producing a sample to be analyzed by a mass spectrometry with matrix assisted laser desorption ionization, in which the rinsing solution is an organic solvent dissolving the matrix compound.

In this invention, since the rinsing solution flow passage is provided to feed the rinsing solution to the tip portion of the probe, the matrix compound deposited at the tip portion of the probe is automatically removed.

With the method for removing the rinsing solution remaining at the tip portion with a cloth, the cloth may be touched with the probe to shift the probe position and make the dripping position inaccurate. However, if a gas is blown from the tip portion of the probe to dry and evaporate the rinsing solution remaining at the tip portion of the probe, after washing, the dripping position of liquid droplet is not shifted, and subsequently the biosample is uniformly fractionated.

DETAILED DESCRIPTION OF THE INVENTION

Figure 1:
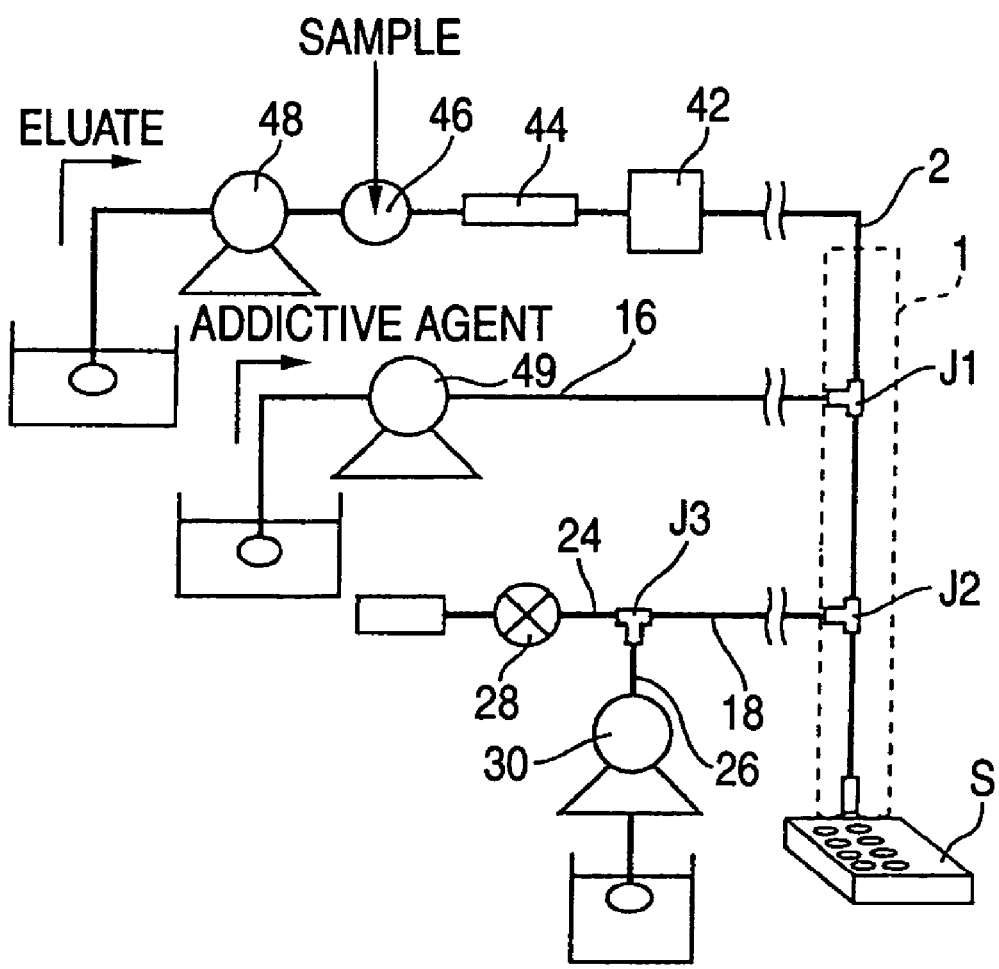
FIG. 1 is a schematic view showing a liquid chromatograph a fractionating apparatus according to one embodiment of the invention.

One embodiment of the present invention will be described below.

The high performance liquid chromatograph comprises a pump 48 for feeding eluate, an injector 46 for injecting a sample, a column 44 for separating the sample constituents, and a detector 42, which are disposed along the flow passage of eluate. A probe 1 for dripping the liquid droplet is connected via a capillary 2 downstream of the detector 42.

The probe 1 comprises the T-type three-way joints J1 and J2, in which an upstream joint J1 connects the capillary 2 for feeding the eluate and a tube 16 for feeding a matrix solution, and a downstream joint J2 connects the capillary 2 and a tube 18 for supplying the air and acetone as rinsing solution, in which a tip portion on the exit side of the probe 1 forms a triple tube structure.

The eluate is fed by the pump 48, and a sample is injected from the injector 46. The sample injected from the injector 46 is separated for each constituent by the column 44, and detected by the detector 42. The eluate is passed through the capillary 2, dripped from the probe 1 onto a sample plate S and captured.

One example of additive agent added to the eluate is a matrix solution. Examples of the matrix compound include nicotinic acid, 2-pyrazine carboxylic acid, sinapic acid (3,5- dimethoxy-4-hydroxycinnamic acid), 2,5-dihydroxybenzoic acid, 5-methoxysalicylic acid, α-cyano-4-hydroxycinnamic acid (CHCA), 3-hydroxypicolinic acid, diaminonaphthalene, 2-(4-hydroxyphenylazo) benzoic acid, dislanol, succinic acid, 5-(trifluoromethyl) uracil, and glycerin.

The rinsing solution for dissolving the matrix compound may be an organic solvent such as acetone or acetonitrile.

Herein, the matrix solution employs a saturated solution (10 mg/mL) in which CHCA (α-cyano-4-hydroxycinnamic acid) is dissolved by a mixed solution of water and acetonitrile, and the rinsing solution employs acetone, for example.

The matrix solution is fed through the tube 16 connected to the capillary 2 via a T-type three-way joint J1 by a pump 49, flowed outside the capillary 2, and dripped together with the eluate containing the sample constituents from the tip portion of the probe 1.

An air supply tube 24 and a rinsing solution supply tube 26 are joined by a T-type three-way joint J3, and a pipe 18 as a common flow passage is connected to the capillary 2 through which the eluate flows and the tube through which the matrix solution flows via a T-type three-way joint J2, whereby the air and rinsing solution flow further outside the tube through which the matrix solution flows. The rinsing solution employs acetone, for example.

A valve 28 is attached to the air supply tube 24, in which the supply of the air is controlled by opening and closing the valve 28. A pump 30 is provided in the rinsing solution supply tube 26, whereby the rinsing solution of acetone is supplied through the rinsing solution supply tube 26 into the probe 1 by operating the pump 30.

In dripping the eluate from the liquid chromatograph, the matrix solution is dripped, together with the eluate, from the tip portion of the probe 1 onto the sample plate S. After dripping the liquid, the matrix compound may deposit on the tip portion of the probe 1, whereby the rinsing solution of acetone is supplied through the rinsing solution supply tube 26 to the tip portion of the probe 1 to rinse the tip portion of the probe 1. To prevent the rinsing solution from remaining on the tip portion after rinsing the tip portion of the probe 1, the valve 28 is opened to supply the air to the tip portion of the probe 1 of the probe 1, and evaporate the rinsing solution remaining on the tip portion of the probe 1.

Figure 2:
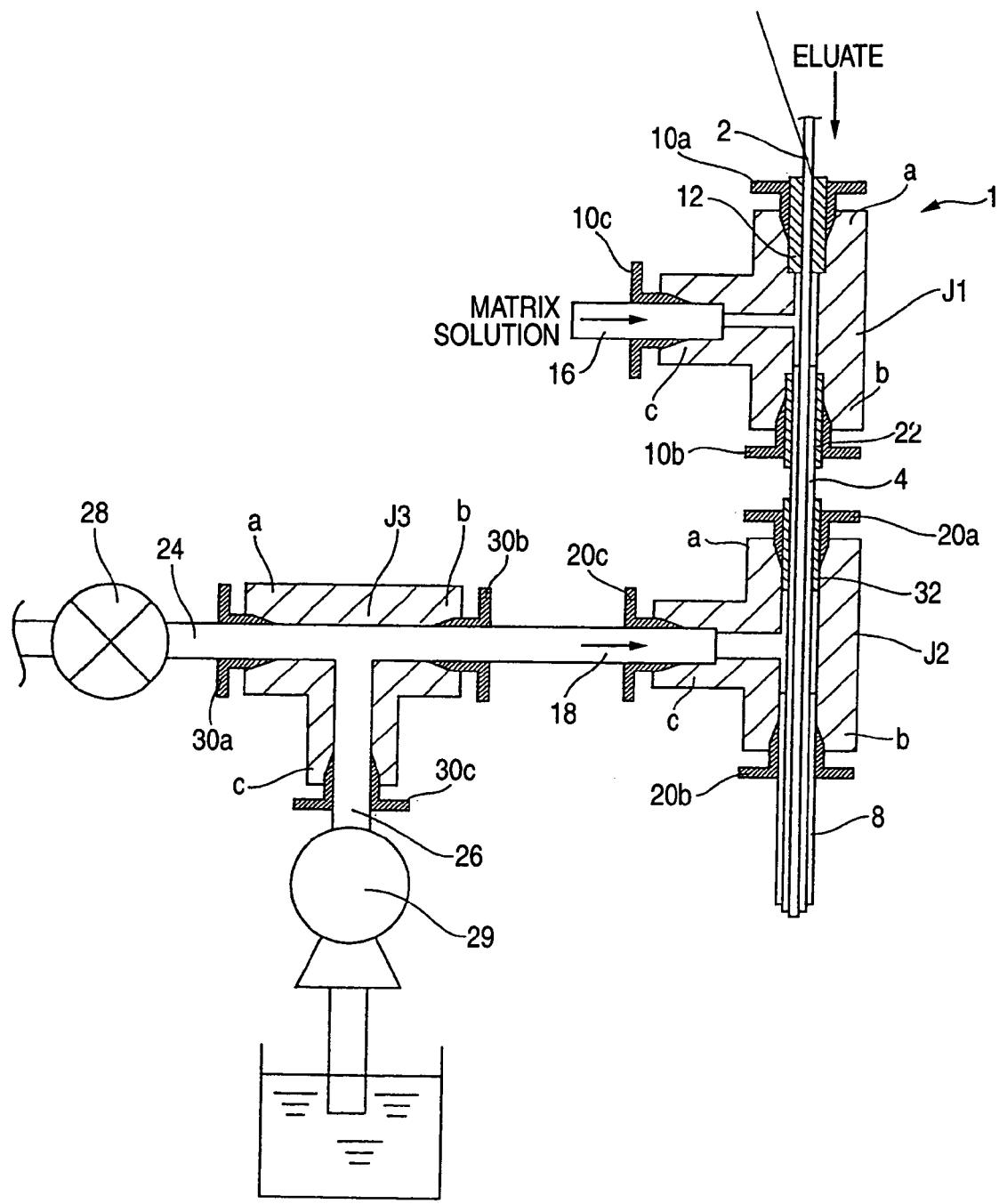
FIG. 2 is a longitudinal cross-sectional view showing in detail the structure of a probe in the embodiment.

FIG. 2 is a longitudinal cross-sectional view showing in detail the structure of a probe in the embodiment.

Two joints a and b, not orthogonal, of the first T-type three-way joint J1 on the upstream side are traversed by the slenderest capillary 2 through which the eluate from the high performance liquid chromatograph is fed. A joint a on the upstream side is tightly sealed via a sleeve 12 by a pipe fitting 10a such as a male nut.

An orthogonal joint c of the T-type three-way joint J1 is connected to the pipe 16 through which the matrix solution is fed, and tightly sealed by a pipe fitting 10c such as a male nut. In a joint b from which the slenderest capillary 2 extends, a capillary 4 is covered over the capillary 2 with a clearance, and tightly sealed via a sleeve 22 by a pipe fitting 10b such as a male nut.

The capillaries 2 and 4 are inserted into the T-type three-way joint J2 on the downstream side from a joint a on the upstream side, and tightly sealed via a sleeve 32 by a pipe fitting 20a such as a male nut. The joint c orthogonal to the capillaries 2 and 4 is connected to the tube 18 for supplying the air and the rinsing solution of acetone, and tightly sealed by a pipe fitting 20c such as a male nut. In a joint b on the most downstream side, a pipe 8 is covered over the capillaries 2 and 4 with a clearance, and tightly sealed by a pipe fitting 20b such as a male nut.

The air supply tube 24 from a joint a, the pipe 18 connected to the T-type three-way joint J2 from a joint b and the rinsing solution supply tube 26 from a joint c are inserted into the T-type three-way joint J3 located sideways of the T-type three-way joint J2, and tightly sealed by the pipe fittings 30a, 30b and 30c such as male nuts.

The air supply tube 24 is provided with the valve 28, whereby the supply of the air to the tip portion of the probe 1 is switched on or off by opening or closing the valve 28. The rinsing solution supply tube 26 is provided with the pump 29, whereby the supply of acetone through the pipe 18 to the tip portion of the probe 1 is switched on or off by turning on or off the operation of the pump 29.

Since the matrix solution is the solution in which the matrix compound of fat-soluble matter is dissolved in solvent at high concentration, if the sample is separated and eluted by the liquid chromatograph, the matrix solution is added simultaneously, and the sample solution is dripped for fractionation, the matrix solution is contact with the atmosphere and the solvent is evaporated at the tip portion of the probe, so that the matrix compound is deposited at the tip portion of the probe.

Thus, the pump 29 is activated to feed acetone by 200 μL, for example, after the end of analysis or before the next analysis, thereby washing the tip portion of the probe 1. Acetone fed by the pump 29 is flowed via the T-type joint J3 for connection with a drying evaporating gas line between the double tube and the triple tube of the probe 1 to rinse away the matrix compound fixed to the tip portion of the probe 1. Thereafter, the drying evaporating gas valve 28 is opened to evaporate residual acetone.

In this embodiment, the air supply tube 24 and the rinsing solution supply tube 26 are manually connected using the T-type joint, in which it is preferable to adjust the flow passage resistance to prevent the rinsing solution of acetone from flowing back to the gas valve 28. For example, the air supply tube 24 may have an inner diameter of 0.1 mm, and a length of about 100 mm.

A three-way electromagnetic valve may be employed, instead of the T-type joint J3, in which it is unnecessary to consider that the rinsing solution flows back to the gas valve 28.

What is claimed is:

1. A fractionating apparatus comprising: a plate, a rinsing solution supply, and a probe for dripping a sample liquid fed from a liquid feed mechanism and an additive agent solution from a tip portion of the probe onto the plate, wherein said probe comprises a rinsing solution flow passage for feeding the rinsing solution from the rinsing solution supply to said tip portion of said probe for dissolving a deposit from said additive agent solution.

2. The fractionating apparatus according to claim 1, wherein the tip portion of said probe has a triple tube structure with an innermost tube, an intermediate tube and an outermost tube, wherein said sample solution flows through the innermost tube, said additive agent solution flows through the intermediate tube outside the innermost tube, and the outermost tube is said rinsing solution flow passage.

3. The fractionating apparatus according to claim 1, wherein said probe has a gas supply flow passage for supplying a gas to said tip portion to dry said tip portion of said probe.

4. The fractionating apparatus according to claim 3, wherein the tip portion of said probe has a triple tube structure with an innermost tube, an intermediate tube and an outermost tube, wherein said sample solution flows through the innermost tube, said additive agent solution flows through the intermediate tube outside the innermost tube, and the outermost tube is used as said rinsing solution flow passage and said gas supply flow passage.

5. The fractionating apparatus according to claim 1, wherein said additive agent solution is a solution of matrix compound for producing a sample to be analyzed by a mass spectrometry with matrix assisted laser desorption ionization, and said rinsing solution is an organic solvent dissolving said matrix compound.

6. The fractionating apparatus according to claim 1, wherein said liquid feed mechanism is a liquid chromatograph.

* * * * *